US011352714B1

United States Patent

(12) United States Patent
Schwartz et al.

(10) Patent No.: US 11,352,714 B1
(45) Date of Patent: Jun. 7, 2022

(54) XSEQ

(71) Applicant: Verily Life Sciences LLC, South San Francisco, CA (US)

(72) Inventors: Jerrod Schwartz, San Francisco, CA (US); Ci Chu, Palo Alto, CA (US); Charles Kim, San Bruno, CA (US); Bi Yu Li, South San Francisco, CA (US); Xiaomi Du, San Francisco, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 420 days.

(21) Appl. No.: 16/293,067

(22) Filed: Mar. 5, 2019

Related U.S. Application Data

(60) Provisional application No. 62/639,122, filed on Mar. 6, 2018.

(51) Int. Cl.

| | |
|---|---|
| ***C40B 40/08*** | (2006.01) |
| ***C12Q 1/686*** | (2018.01) |
| ***G01N 33/68*** | (2006.01) |
| ***C40B 20/02*** | (2006.01) |
| ***C12Q 1/6806*** | (2018.01) |

(52) U.S. Cl.
CPC .............. *C40B 40/08* (2013.01); *C12Q 1/686* (2013.01); *C12Q 1/6806* (2013.01); *C40B 20/02* (2013.01); *G01N 33/6857* (2013.01)

(58) Field of Classification Search
None
See application file for complete search history.

(56) References Cited

U.S. PATENT DOCUMENTS

2010/0120098 A1 5/2010 Grunenwald et al.
2013/0203605 A1 8/2013 Shendure et al.
2018/0024139 A1* 1/2018 Peikon et al. ....... C12Q 1/6804 506/4

FOREIGN PATENT DOCUMENTS

WO 2017124101 7/2017

OTHER PUBLICATIONS

Hou et al., "Single-cell triple omics sequencing reveals genetic, epigenetic, and transcriptomic heterogeneity in hepatocellular carcinomas," Cell Res. 2016, 26:304-319. (Year: 2016).*

Adey et al., "Rapid, low-input, low-bias construction of shotgun fragment libraries by high-density in vitro transposition," Genome Biol. 2010, 11:R119. (Year: 2010).*

"An Overview of Recent Single-cell Research Publications Featuring Illumina Technology", Illumina, Single-cell Research, Oct. 24, 2016, 93 pages.

Ackermann et al., "Integration of ATAC-seq and RNA-seq Identifies Human Alpha Cell and Beta Cell Signature Genes", Mol Metab., vol. 5, No. 3, Jan. 11, 2016, pp. 233-244.

Adey et al., "Rapid, low-input, low-bias construction of shotgun fragment libraries by high-density in vitro transposition", Genome Biology, vol. 11, No. 12, 2010, pp. 1-17.

Caruccio , "Preparation of Next-generation Sequencing Libraries Using Nextera™ Technology: Simultaneous DNA Fragmentation and Adaptor Tagging by in Vitro Transposition", Methods In Molecular Biology, Humana Press. Inc., vol. 733, Feb. 2011, pp. 241-255.

Deangelis et al., "An Overview of Epigenetic Assays", Mol Biotechnol., vol. 38, No. 2, Feb. 2008, pp. 179-183.

Hou et al., "Single-cell triple omics sequencing reveals genetic, epigenetic, and transcriptomic heterogeneity in hepatocellular carcinomas", Cell Research, vol. 26, No. 3, Mar. 2016, pp. 304-319.

Khyzha et al., "Epigenetics of Atherosclerosis: Emerging Mechanisms and Methods", Trends Mol Med., vol. 23, No. 4, Apr. 2017, pp. 332-347 (abstract only).

Kozlov et al., "Efficient strategies for the conjugation of oligonucleotides to antibodies enabling highly sensitive protein detection", Biopolymers 73.5 (2004): 621-630 (abstract only).

Picelli et al., "Tn5 transposase and tagmentation procedures for massively scaled sequencing projects", Genome Research, vol. 24, No. 12, Dec. 2014, pp. 2033-2040.

* cited by examiner

*Primary Examiner* — Kaijiang Zhang
(74) *Attorney, Agent, or Firm* — Kilpatrick Townsend & Stockton LLP

(57) ABSTRACT

Provided herein are methods for identification of an expression profile, a transcriptional profile, and/or an epigenetic profile from a cell-containing sample. Also provided are compositions for use in the disclosed methods.

22 Claims, 6 Drawing Sheets

Specification includes a Sequence Listing.

| | Mars26_RNA_3F | Mars26_RNA_3G | Mars26_RNA_3B | Mars26_RNA_3C | Mars26_RNA_3A | Mars26_RNA_3D | Mars26_RNA_1D | Mars26_RNA_1B | Mars26_RNA_1F | Mars26_RNA_1E | Mars26_RNA_1C | Mars26_RNA_1G |
|---|---|---|---|---|---|---|---|---|---|---|---|---|
| Mars26_RNA_3F | 1.00 | 0.84 | 0.84 | 0.83 | 0.84 | 0.84 | 0.77 | 0.78 | 0.77 | 0.78 | 0.78 | 0.79 |
| Mars26_RNA_3G | 0.84 | 1.00 | 0.84 | 0.84 | 0.84 | 0.84 | 0.77 | 0.78 | 0.77 | 0.78 | 0.78 | 0.79 |
| Mars26_RNA_3B | 0.84 | 0.84 | 1.00 | 0.84 | 0.84 | 0.85 | 0.77 | 0.78 | 0.77 | 0.78 | 0.78 | 0.79 |
| Mars26_RNA_3C | 0.83 | 0.84 | 0.84 | 1.00 | 0.84 | 0.84 | 0.77 | 0.78 | 0.77 | 0.78 | 0.78 | 0.78 |
| Mars26_RNA_3A | 0.84 | 0.84 | 0.84 | 0.84 | 1.00 | 0.85 | 0.77 | 0.78 | 0.77 | 0.78 | 0.79 | 0.79 |
| Mars26_RNA_3D | 0.84 | 0.84 | 0.85 | 0.84 | 0.85 | 1.00 | 0.77 | 0.78 | 0.77 | 0.78 | 0.79 | 0.79 |
| Mars26_RNA_1D | 0.77 | 0.77 | 0.77 | 0.77 | 0.77 | 0.77 | 1.00 | 0.80 | 0.79 | 0.80 | 0.81 | 0.81 |
| Mars26_RNA_1B | 0.78 | 0.78 | 0.78 | 0.78 | 0.78 | 0.78 | 0.80 | 1.00 | 0.80 | 0.80 | 0.81 | 0.81 |
| Mars26_RNA_1F | 0.77 | 0.77 | 0.77 | 0.77 | 0.77 | 0.77 | 0.79 | 0.80 | 1.00 | 0.80 | 0.81 | 0.81 |
| Mars26_RNA_1E | 0.78 | 0.78 | 0.78 | 0.78 | 0.78 | 0.78 | 0.80 | 0.80 | 0.80 | 1.00 | 0.81 | 0.81 |
| Mars26_RNA_1C | 0.78 | 0.78 | 0.78 | 0.78 | 0.79 | 0.79 | 0.81 | 0.81 | 0.81 | 0.81 | 1.00 | 0.82 |
| Mars26_RNA_1G | 0.79 | 0.79 | 0.79 | 0.78 | 0.79 | 0.79 | 0.81 | 0.81 | 0.81 | 0.81 | 0.82 | 1.00 |

| | Mars26_ImATAC_3F | Mars26_ImATAC_3G | Mars26_ImATAC_3C | Mars26_ImATAC_3D | Mars26_ImATAC_3A | Mars26_ImATAC_3B | Mars26_ImATAC_1D | Mars26_ImATAC_1E | Mars26_ImATAC_1F | Mars26_ImATAC_1B | Mars26_ImATAC_1C | Mars26_ImATAC_1G |
|---|---|---|---|---|---|---|---|---|---|---|---|---|
| Mars26_ImATAC_3F | 1.00 | 0.88 | 0.88 | 0.88 | 0.88 | 0.88 | 0.50 | 0.49 | 0.49 | 0.49 | 0.50 | 0.50 |
| Mars26_ImATAC_3G | 0.88 | 1.00 | 0.89 | 0.89 | 0.88 | 0.88 | 0.50 | 0.49 | 0.49 | 0.49 | 0.50 | 0.50 |
| Mars26_ImATAC_3C | 0.88 | 0.89 | 1.00 | 0.89 | 0.88 | 0.88 | 0.50 | 0.50 | 0.50 | 0.50 | 0.50 | 0.50 |
| Mars26_ImATAC_3D | 0.88 | 0.89 | 0.89 | 1.00 | 0.88 | 0.88 | 0.50 | 0.49 | 0.49 | 0.49 | 0.50 | 0.49 |
| Mars26_ImATAC_3A | 0.88 | 0.88 | 0.88 | 0.88 | 1.00 | 0.88 | 0.50 | 0.50 | 0.50 | 0.50 | 0.50 | 0.50 |
| Mars26_ImATAC_3B | 0.88 | 0.88 | 0.88 | 0.88 | 0.88 | 1.00 | 0.50 | 0.50 | 0.50 | 0.50 | 0.50 | 0.50 |
| Mars26_ImATAC_1D | 0.50 | 0.50 | 0.50 | 0.50 | 0.50 | 0.50 | 1.00 | 0.87 | 0.87 | 0.87 | 0.87 | 0.87 |
| Mars26_ImATAC_1E | 0.49 | 0.49 | 0.50 | 0.49 | 0.50 | 0.50 | 0.87 | 1.00 | 0.87 | 0.87 | 0.87 | 0.87 |
| Mars26_ImATAC_1F | 0.49 | 0.49 | 0.50 | 0.49 | 0.50 | 0.50 | 0.87 | 0.87 | 1.00 | 0.87 | 0.87 | 0.87 |
| Mars26_ImATAC_1B | 0.49 | 0.49 | 0.50 | 0.49 | 0.50 | 0.50 | 0.87 | 0.87 | 0.87 | 1.00 | 0.88 | 0.88 |
| Mars26_ImATAC_1C | 0.50 | 0.50 | 0.50 | 0.50 | 0.50 | 0.50 | 0.87 | 0.87 | 0.87 | 0.88 | 1.00 | 0.88 |
| Mars26_ImATAC_1G | 0.50 | 0.50 | 0.50 | 0.49 | 0.50 | 0.50 | 0.87 | 0.87 | 0.87 | 0.88 | 0.88 | 1.00 |

Figure 3

Oligo Set 1 (1 universal) Total= 50 nt:

| 5' Am | Tn5ME-A (sense, 33nt) | | ImmunoPCR assay ID (17nt) | 3' |
|---|---|---|---|---|
| | TCGTCGGCAGCGTC | AGATGTGTATAAGAGACAG | GCAGTGTGCCTTCATTC | |

Oligo Set 2: total= 65 nt

| 5' | Tn5ME-B (34nt)_REV | | Antibody BC (6nt)_REV | UMI (8nt) | ImmunoPCR assay ID (17 bp)_REV | |
|---|---|---|---|---|---|---|
| desBiotin | GTCTCGTGGGCTCGG | AGATGTGTATAAGAGACAG | NNNNNN | nnnnnnnn | GAATGAAGGCACACTGC | |

Figure 6

XSEQ

CROSS-REFERENCE TO RELATED APPLICATION

The present application claims the benefit of priority to U.S. Provisional Application No. 62/639,122, filed on Mar. 6, 2018, the entire contents of which are incorporated by reference herein for all purposes.

FIELD

Embodiments of the present disclosure relate to the identification of an expression profile, an epigenetic profile and/or a transcriptional profile of a cell-containing sample. In particular, compositions and methods for identifying an expression profile, an epigenetic profile and/or a transcriptional profile of a single cell or a population of cells are provided.

BACKGROUND

Although recent developments in next generation sequencing allow analysis of the epigenome, the transcriptome, and the proteome of a sample, these assays usually destroy the sample in the process, precluding inter-assay compatibility. As a result, replicate aliquots must be prepared for multiplexed analysis, often doubling or tripling sample preparation time. This puts further constraints on sample availability and makes inter-assay comparisons from the same sample difficult, if not impossible. Therefore, the field lacks a practical solution for simultaneously analyzing the epigenome, the transcriptome, and the proteome of a sample that is quantitative and reproducible.

SUMMARY

Provided herein are methods for biochemical analysis of a cell-containing sample, including the step of contacting a cell-containing sample with a plurality of antigen-binding molecules under conditions that promote specific binding of the antigen-binding molecules to target antigens of the cells in the sample, wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, an (ii) an antigen-binding molecule identifier sequence corresponding to the unique target antigen, and (iii) an assay molecule identifier sequence. Further, the method may include tagmenting genomic DNA in the cells to produce a plurality of tagmented double-stranded genomic DNA fragments comprising an oligonucleotide adaptor sequence at the 5' end of each genomic DNA fragment. The method may further include lysing the cells in the sample. Also, the method may include isolating mRNA transcripts from the cell lysate to produce a first fraction comprising the mRNA transcripts and a second fraction comprising tagmented genomic DNA fragments and the antigen-binding molecule-bound antigens from the cell lysate. The method also may include generating a cDNA library by reverse transcribing the mRNA transcripts in the first fraction. Further, the method may include amplifying (i) the unique molecular identifier sequences; (ii) the antigen-binding molecule identifier sequences; (iii) the assay molecule identifier sequences, and the (iv) tagmented genomic DNA fragments in the second fraction. Also, the method may include analyzing the amplified unique molecular identifier sequences and antigen-binding molecule identifier sequences to identify at least one target antigen in the second fraction to identify the expression profile of the sample. The method further may include analyzing the genomic DNA fragments in the second fraction to identify the epigenetic profile of the sample. Also, the method may include analyzing the cDNA library generated from the first fraction to identify the transcriptional profile of the sample.

In some embodiments, the method further comprises quantifying the amplified unique molecular identifier sequences, the antigen-binding molecule identifier sequences, the assay molecule identifier sequences, and/or the tagmented genomic DNA fragments in the second fraction. In some embodiments, the method further comprises using solid phase reversible immobilization to isolate tagmented genomic DNA fragments prior to amplification. In some embodiments, the tagmented genomic DNA fragments are amplified and/or sequenced using one or more primers that hybridize to the oligonucleotide adaptor at the 5' end of the fragment. In some embodiments, one or more analyzing steps comprise sequencing the amplified unique molecular identifier sequences, the antigen-binding molecule identifier sequences, the assay molecular identifier sequences, and the genomic fragments in the second fraction. In some embodiments, the amplification products from the first and/or second fractions are pooled prior to sequencing. In some embodiments, the antigen is a protein. In specific embodiments, the protein is a cell surface protein or an intracellular protein. In some embodiments, the expression of two or more proteins are identified. In some embodiments, amplification is performed by polymerase chain reaction (PCR). In some embodiments, sequencing comprises sequence by synthesis. In some embodiments, sequencing comprises high throughput sequencing. In some embodiments, the unique molecular identifier sequence is between about five and about fifty nucleotides in length. In some embodiments, the antigen-binding molecule identifier sequence is between about five and about fifty nucleotides in length. In some embodiments, the plurality of antigen-binding molecules comprises between two and about five hundred distinct antigen-binding molecules. In some embodiments, the method further comprises tagmenting the cDNA library to produce a plurality of double-stranded cDNA fragments comprising an oligonucleotide adaptor sequence at the 5' end of each cDNA fragment prior to analyzing. In some embodiments, the mRNA transcripts are isolated from the cell lysate by allowing hybridization of the mRNA transcripts in the cell lysate with beads comprising poly (dT) sequences. In some embodiments, the cell-containing sample is treated with Proteinase K prior to or concurrently with the lysing of the cells in the sample. In some embodiments, the cell-containing sample is a population of cells. In some embodiments, single cells of the population are separated into individual compartments prior to lysing the single cell in each compartment. In some embodiments, an expression profile, an epigenetic profile and a transcriptional profile are identified for the single cell or population of cells. In some embodiments, the individual compartments are wells of a tissue culture plate. In some embodiments, the single cells separated into individual compartments are single cells from a subpopulation of the population of cells contacted with the plurality of antigen-binding molecules. In some embodiments, the subpopulation of cells is isolated from the population of cells contacted with the plurality of antigen-binding molecules prior to separating single cells of the subpopulation into separate compartments. In some embodiments, the subpopulation is isolated using fluorescence activated cell sorting (FACS) or magnetic-activated cell sorting (MACS). In some embodiments, the antigen-binding molecule is an antibody.

Also provided are methods for biochemical analysis of a cell-containing sample, including the step of contacting a cell-containing sample with a plurality of antigen-binding molecules under conditions that promote specific binding of the antigen-binding molecules to target antigens of the cells in the sample; wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, (ii) an antigen-binding molecule identifier sequence corresponding to the unique target antigen, and (iii) an assay molecular identifier sequence. Further, the method may include tagmenting genomic DNA of the cell(s) to produce a plurality of double-stranded genomic DNA fragments comprising an oligonucleotide adaptor sequence at the 5' end of each genomic DNA fragment. Also, the method may include amplifying (i) the unique molecular identifier sequences, (ii) the antigen-binding molecule identifier sequences, and (iii) the assay molecular identifier sequence in the cell(s). The method also may include lysing the cells in the sample. Further, the method may include analyzing the amplified unique molecular identifier sequences, the antigen-binding molecule identifier sequences, and the assay molecular identifier sequences to identify at least one target antigen to identify the expression profile in the sample. Also, the method may include analyzing the genomic DNA fragments to identify the epigenetic profile of the sample.

In some embodiments, the method further comprises quantifying the amplified unique molecular identifier sequences, the assay molecular identifier sequences and the antigen-binding molecule identifier sequences. In some embodiments, the method further comprises using solid phase reversible immobilization to isolate DNA fragments prior to amplification. In some embodiments, the tagmented genomic DNA fragments are amplified and/or sequenced using one or more primers that hybridize to the oligonucleotide adaptor sequence at the 5' end of each tagmented genomic DNA fragment. In some embodiments, analyzing comprises sequencing the amplified unique molecular identifier sequences, the antigen-binding molecule identifier sequences, the assay molecular identifier sequences and the genomic fragments. In some embodiments, the amplification products are pooled prior to sequencing. In some embodiments, the antigen is a protein. In specific embodiments, the protein is a cell surface protein or an intracellular protein. In some embodiments, the expression of two or more proteins are identified. In some embodiments, amplification is performed by polymerase chain reaction (PCR). In some embodiments, sequencing comprises sequence by synthesis. In some embodiments, sequencing comprises high throughput sequencing. In some embodiments, the unique molecular identifier sequence is between about five and about fifty nucleotides in length. In some embodiments, the antigen-binding molecule identifier sequence is between about five and about fifty nucleotides in length. In some embodiments, the plurality of antigen-binding molecules comprises between two and about five hundred distinct antigen-binding molecules. In some embodiments, the cell-containing sample is treated with Proteinase K prior to or concurrently with the lysing of the cells in the sample. In some embodiments, the cell-containing sample is a population of cells. In some embodiments, single cells of the population are separated into individual compartments prior to lysing the single cell in each compartment. In some embodiments, an expression profile and an epigenetic profile are identified for the single cell or population of cells. In some embodiments, the individual compartments are wells of a tissue culture plate. In some embodiments, the single cells separated into individual compartments are single cells from a subpopulation of the population of cells contacted with the plurality of antigen-binding molecules. In some embodiments, the subpopulation of cells is isolated from the population of cells contacted with the plurality of antigen-binding molecules prior to separating single cells of the subpopulation into individual compartments. In some embodiments, the subpopulation is isolated using FACS or MACS. In some embodiments, the antigen-binding molecule is an antibody.

Also provided are methods for biochemical analysis of a cell-containing sample, including the step of lysing the cells in the sample. The method also may include tagmenting genomic DNA in the cell lysate to produce a plurality of double-stranded genomic DNA fragments comprising an oligonucleotide adaptor sequence at the 5' end of each genomic DNA fragment. Further, the method may include isolating mRNA transcripts from the cell lysate to produce a first fraction comprising the mRNA transcripts and a second fraction comprising the tagmented genomic DNA fragments. The method may also include generating a cDNA library by reverse transcribing the mRNA transcripts in the first fraction. Further, the method may include amplifying the tagmented genomic DNA fragments in the second fraction. Also, the method may include analyzing the tagmented genomic DNA fragments in the second fraction to identify the epigenetic profile of the sample. Further, the method may include analyzing the cDNA library generated from the first fraction to identify the transcriptional profile of the sample.

In some embodiments, the method further comprises using solid phase reversible immobilization to isolate tagmented genomic DNA fragments prior to amplification. In some embodiments, the tagmented genomic DNA fragments are amplified and/or sequenced using one or more primers that hybridize to the oligonucleotide adaptor sequence at the 5' end of each fragment. In some embodiments, the amplification products are pooled prior to sequencing. In some embodiments, amplification is performed by polymerase chain reaction (PCR). In some embodiments, sequencing comprises sequence by synthesis. In some embodiments, sequencing comprises high throughput sequencing. In some embodiments, the cell-containing sample is a population of cells. In some embodiments, single cells of the population are separated into individual compartments prior to lysing the single cell in each compartment. In some embodiments, an epigenetic profile and a transcriptional profile are identified for the single cell. In some embodiments, the individual compartments are wells of a tissue culture plate. In some embodiments, the single cells separated into individual compartments are single cells from a subpopulation of the population of cells. In some embodiments, the subpopulation of cells is isolated from the population of cells prior to separating single cells of the subpopulation into individual compartments. In some embodiments, the subpopulation is isolated using fluorescence FACS or MACS.

DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 3 shows a correlation table for the results of epigenetic profiling. Results for Assay for Transposase-Accessible Chromatin using sequencing (ATACseq) peak correlation are shown for the samples as listed across the left and top of the figure. Sample nomenclature appear in this figure as "Sample [subset ID #][replicate #]." Peak correlation between sample replicates for ATACseq is about 0.9 for a good sample. In the correlation table, the correlation between replicates of Subset 1 is about 0.87. Correlation between replicates of subset 2 is about 0.88. Since subset 1 and subset 2 are two distinct subsets, correlation between samples of subset 1 and subset 2 is expected to be low, which is supported by the data (correlation is about 0.5 between the two subsets).

FIG. 6 is a schematic diagram showing an example of a two-component oligonucleotide for use in the methods described herein. The first component, Oligo Set 1 (SEQ ID NO: 1), contains a PCR primer and an assay molecular identifier sequence. The second component, Oligo Set 2 (SEQ II) NO: 2), contains an antigen-binding molecule identifier sequence (antibody BC), a unique molecular identifier sequence (UMI), and the reverse complement of the assay molecular identifier sequence of Oligo Set 1.

DETAILED DESCRIPTION

Figure 1:
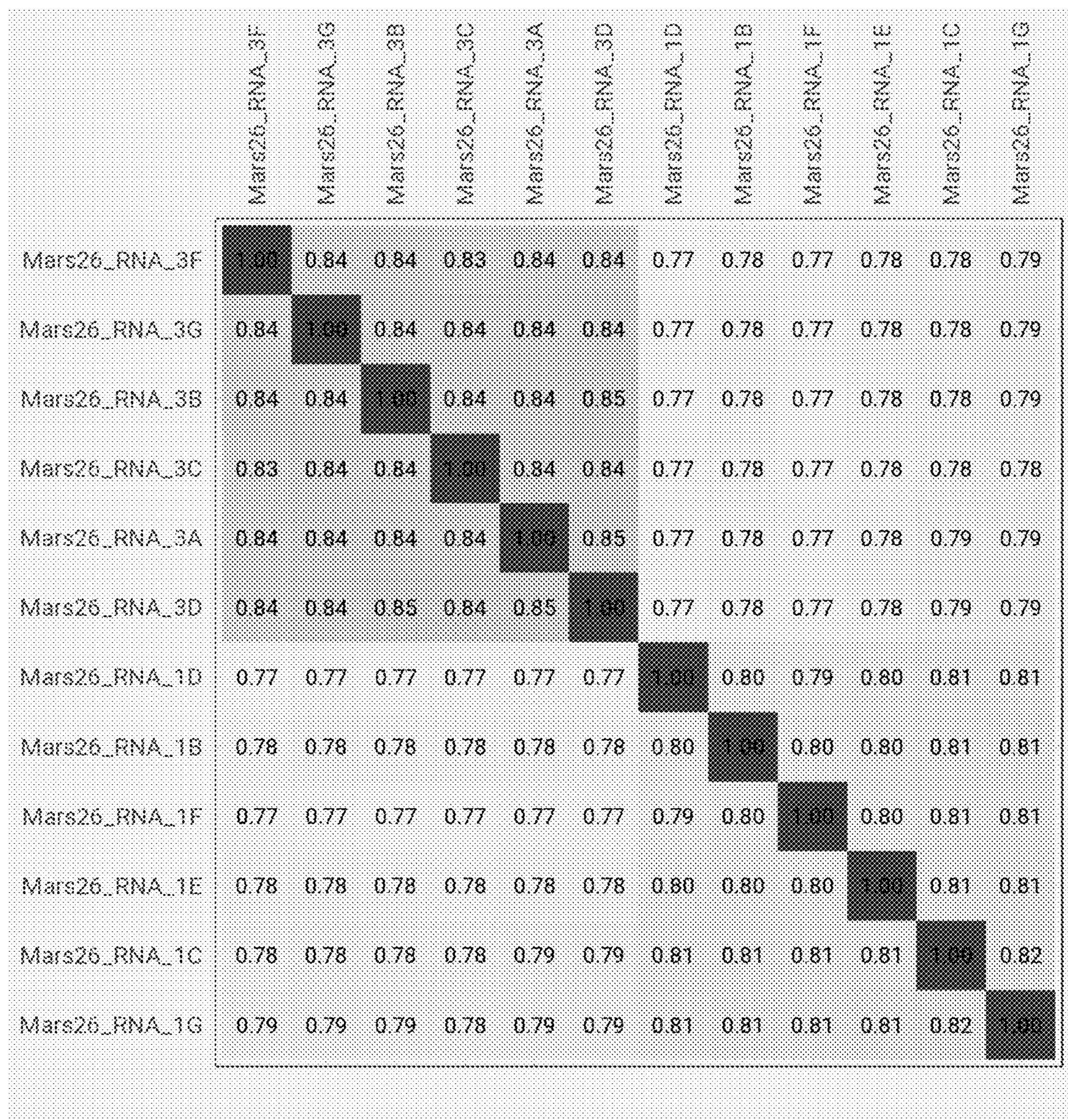
FIG. 1 shows the results of RNAseq (transcriptional profiling) experiments. RNA expression correlation is shown for the samples as listed across the left and top of the figure. Sample nomenclature appear in this figure as "Sample [subset ID #] [replicate #]." Correlation among technical replicates (e.g., between replicates 3A-3G or between replicates 1B-1G) is higher than correlation between different cell types (e.g., between replicates of subset 1 and replicates of subset 2).

The following description recites various aspects and embodiments of the present compositions and methods. No particular embodiment is intended to define the scope of the compositions and methods. Rather, the embodiments merely provide non-limiting examples that are at least included within the scope of the disclosed compositions and methods. The description is to be read from the perspective of one of ordinary skill in the art; therefore, information well known to the skilled artisan is not necessarily included.

Provided herein are compositions and methods for the biochemical analysis of a cell-containing sample. These include methods for identifying an expression profile, a transcriptional profile and/or an epigenetic profile of a cell-containing sample. Certain methods include the steps of a) contacting a cell-containing sample with a plurality of antigen-binding molecules under conditions that promote specific binding of the antigen-binding molecules to target antigens of the cells in the sample; wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, an (ii) an antigen-binding molecule identifier sequence corresponding to the unique target antigen; and (iii) an assay molecular identifier sequence; b) tagmenting genomic DNA in the cells in the sample to produce a plurality of double-stranded genomic DNA fragments comprising an oligonucleotide adaptor sequence at the 5' end of each genomic DNA fragment; c) lysing the cells in the sample; d) isolating mRNA transcripts from the cell lysate to produce a first fraction comprising the mRNA transcripts and a second fraction comprising tagmented genomic DNA fragments and the antigen-binding molecule-bound antigens from the cell lysate; e) generating a cDNA library by reverse transcribing the mRNA transcripts in the first fraction; f) amplifying (i) the unique molecular identifier sequences; (ii) the antigen-binding molecule identifier sequences; (iii) the assay molecular identifier sequences, and (iv) the tagmented genomic DNA fragments in the second fraction; g) analyzing the amplified unique molecular identifier sequences, the assay molecular identifier sequences, and antigen-binding molecule identifier sequences to identify at least one target antigen in the second fraction to identify the expression profile of the sample; h) analyzing the tagmented genomic DNA fragments in the second fraction to identify the epigenetic profile of the sample; and i) analyzing the cDNA library generated from the first fraction to identify the transcriptional profile of the sample.

Biochemical analysis of any cell-containing sample can be performed using any of the compositions and methods provided herein. In some embodiments, the cell-containing sample may be from a tissue sample. For example, the tissue sample may be from an animal or a plant. Optionally, the cell-containing sample, is from a mammalian subject, for example, a human subject. The cell-containing sample may be obtained from any part of the subject, for example, from the blood, skin, or organ(s) of the subject. For example, and not to be limiting, the sample may be a biopsy sample from the brain, muscle, liver, pancreas, breast, a reproductive organ, lung, oral cavity, bladder, esophagus, kidney, prostate, bone, spinal cord, skin, stomach, or gastrointestinal tract of the subject. The cell-containing sample may be from a tumor. The cell-containing sample may be from cancerous tissue or from non-cancerous tissue. The cell-containing sample may be from a healthy subject or from a subject with a particular disease or disorder.

In some embodiments, the cell-containing sample is a population of cells or a single cell. Subpopulations of cells isolated from populations of cells, for example, using FACS or MACS, also can be analyzed using the methods provided herein. In the methods provided herein, the cell in the cell-containing sample can be a eukaryotic cell, a prokaryotic cell, an animal cell, a plant cell, a fungal cell, and the like. Optionally, the cell is a mammalian cell, for example, a human cell. The cell can be from a bodily fluid, tissue, or organ. The cell also may be a primary cell, a germ cell, a stem cell, or a precursor cell. The precursor cell can be, for example, a pluripotent stem cell or a hematopoietic stem cell. The cell can also be a totipotent or multipotent stem cell. Biochemical analysis of a cell in a particular phase of the cell cycle also may be determined. One of skill in the art would know how to synchronize cells to increase a proportion of cells in a particular phase prior to determination of the expression profile of the cell. The cell can be a cell from a healthy subject or a subject with a disease. In some embodiments, the population of cells is from one or more subjects. In some embodiments, the population of cells is a heterogeneous population of cells (i.e., a mixture of different cell types) or a homogeneous population of cells. In some embodiments, the population contains at least two different cell types. In some embodiments, the cells in the population include healthy and/or diseased cells from a thymus, white blood cells, red blood cells, liver cells, spleen cells, lung cells, heart cells, brain cells, skin cells, pancreas cells, stomach cells, cells from the oral cavity, cells from the nasal cavity, colon cells, small intestine cells, kidney cells, cells from a gland, brain cells, neural cells, glial cells, eye cells, reproductive organ cells, bladder cells, gamete cells, human cells, fetal cells, amniotic cells, or any combination thereof.

As used throughout, the term "subject" refers to an individual. Preferably, the subject is a mammal such as a primate, and, more preferably, a human of any age, including a newborn or a child. Non-human primates may be subjects as well. The term subject also may include domesticated animals (e.g., cats, dogs), livestock (e.g., cattle, horses, pigs, sheep, goats), and laboratory animals (e.g., ferret, chinchilla, mouse, rabbit, rat, gerbil, guinea pig). Thus, veterinary uses are contemplated herein.

As used throughout, an "expression profile" or an "antigen expression profile" provides information about target antigens that are present in a cell-containing sample. In some embodiments, the antigens are produced by a cell(s) in the cell-containing sample. As used throughout, the phrase "target antigens" may include, for example, proteins, lipids, or sugars. A target antigen may be measured using an affinity reagent. The expression profile may include the identity of one or more target antigens in the cell-containing sample, and/or the amount (relative or absolute) of one or more target antigens in the cell-containing sample. The expression profile also may include the amount of a first target antigen relative to the amount of a different, second target antigen. The expression profile also may include information about target antigens that are not expressed in the cell-containing sample. In some embodiments, the target antigen is a protein. A wide variety of proteins may be considered antigens. Such proteins include, but are not limited to, immunoglobulins, cytokines, enzymes, hormones, cancer antigens, receptors, nutritional markers, and tissue specific antigens. The protein can be an intracellular protein, a cell-surface protein, or an extracellular protein. In some embodiments, the expression profile includes the identity, and/or the amount of cell-surface proteins. In other embodiments, the expression profile includes the identity, and/or amount of cell-surface proteins and intracellular proteins in the cell-containing sample. In other embodiments, the expression profile includes the identity and/or amount of cell-surface proteins, intracellular proteins, and extracellular proteins in the cell-containing sample. In some embodiments, the expression of two or more antigens are identified. For example, the expression of 10, 25, 50, 100, 200, 300, 400, 500, 600, 700, 800, 900, 1,000, 2,000, 3,000, 4,000, 5,000, 6,000, 7,000, 8,000, 9000, 10000, 20,000, or more antigens, for example, proteins, may be identified in the expression profile.

As used throughout, a "transcriptional profile" provides information about nucleic acid expression in a cell-containing sample. The transcriptional profile may include the identity of one or more mRNAs that are expressed in the cell-containing sample, and/or the amount (relative or absolute) of one or more mRNAs in the cell-containing sample. The transcriptional profile also may include the amount of a first mRNA relative to the amount of a different, second mRNA. The transcriptional profile also may include information about mRNAs that are not expressed in the cell-containing sample. In some embodiments, a transcriptional profile is obtained by generating a cDNA library, for example, by reverse transcribing mRNA transcripts from the cell-containing sample, and analyzing the cDNA library. mRNAs encode a wide variety of proteins, such as, but are not limited to, immunoglobulins, cytokines, enzymes, hormones, cancer antigens, receptors, nutritional markers, and tissue specific antigens. The protein encoded by the mRNA can be an intracellular protein, a cell-surface protein, or an extracellular protein. In some embodiments, the transcriptional profile includes the identity, and/or the amount of mRNAs encoding cell-surface proteins. In other embodiments, the transcriptional profile includes the identity and/or amount of mRNAs encoding cell-surface proteins and intracellular proteins in the cell-containing sample. In other embodiments, the transcriptional profile includes the identity and/or amount of mRNAs encoding cell-surface proteins, intracellular proteins, and extracellular proteins in the cell-containing sample. In some embodiments, two or more mRNAs are identified in the transcriptional profile. For example, the expression of 10, 25, 50, 100, 200, 300, 400, 500, 600, 700, 800, 900, 1,000, 2,000, 3,000, 4,000, 5,000, 6,000, 7,000, 8,000, 9000, 10000, 20,000, or more mRNAs may be identified in the transcriptional profile.

As used throughout, an "epigenetic profile" provides information about gene expression that is not due to changes in the genomic sequence of a cell or organism. Examples of epigenetic modifications that can influence gene expression without altering a genomic sequence include, but are not limited to, DNA methylation status, histone modification status, and nucleosome positioning, to name a few. Therefore, an epigenetic profile can contain information about epigenetic modifications to one or more genomic sequences in the cell-containing sample. In some embodiments, the epigenetic profile includes the identity of one or more genomic DNA fragments, and/or epigenetic modifications, if any, to the one or more genomic fragments. For example, the epigenetic status of about 10, 25, 50, 100, 200, 300, 400, 500, 600, 700, 800, 900, 1,000, 2,000, 3,000, 4,000, 5,000, 6,000, 7,000, 8,000, 9000, 10000, 20,000, or more genomic fragments may be identified in the epigenetic profile. Methods for identifying and analyzing epigenetic modifications of genomic DNA fragments are known in the art. See, for example, DeAngelis and Farrington, *Mol. Biotechnol.* 38(2): 179-183 (2008); and Khyzha et al. *Trends in Molecular Medicine* 23(4):332-347 (2017).

In some embodiments, an expression profile, a transcriptional profile, and/or an epigenetic profile obtained using the methods provided herein can be used to diagnose a disease or condition in a subject or to determine how a subject will respond to treatment. In some embodiments, the presence of a specific expression profile, transcriptional profile, and/or epigenetic profile associated with a particular disease or disorder may be used to diagnose and treat a subject with the disease or disorder. In other embodiments, the presence of a specific expression profile, transcriptional profile, and/or epigenetic profile may be used to determine if the subject is at risk for developing the disease or disorder.

In some embodiments, the expression profile, transcriptional profile, and/or epigenetic profile of a cell-containing sample can be compared with a reference expression profile transcriptional profile, and/or epigenetic profile of a cell-containing sample. For example, the expression profile, transcriptional profile, and/or epigenetic profile of a cell-containing sample that has been treated with an agent can be compared with the expression profile, transcriptional profile, and/or epigenetic profile of a cell-containing sample prior to treatment to determine if treatment has altered or modulated the expression profile, transcriptional profile, and/or epigenetic profile of a cell-containing sample. In another example, the expression profile, transcriptional profile, and/or epigenetic profile of a cell-containing sample from a subject being treated for a disease can be compared with the expression profile, transcriptional profile, and/or epigenetic profile of a cell-containing sample from a healthy subject that does not have the disease, or can be compared with the expression profile, transcriptional profile, and/or epigenetic profile of a cell-containing sample from a subject that has been successfully treated for the disease. In another example, the expression profile, transcriptional profile, and/or epigenetic profile of a cell-containing sample comprising cells at a particular point in the cell cycle can be compared with the expression profile, transcriptional profile, and/or epigenetic profile of a cell-containing sample comprising cells at a different point in the cell cycle.

As used throughout, the phrase "multiple antigen-binding molecules" means two or more antigen-binding molecules. It is understood that the term "multiple" is used interchangeably with the phrase "a plurality of." As used herein, an antigen-binding molecule is a molecule that has a binding affinity for an antigen, optionally a specific binding affinity and may include, but is not limited to, an antibody, an aptamer, or a small molecule. As used throughout, the term "antibody" encompasses, but is not limited to, a nanobody, a whole immunoglobulin (i.e., an intact antibody) of any class, including polyclonal and monoclonal antibodies, as well as fragments of antibodies that retain the ability to bind their specific antigens. Also useful as antigen-binding molecules in the methods provided herein are conjugates of antibody fragments and antigen-binding proteins (single chain antibodies) as described, for example, in U.S. Pat. No. 4,704,692, the contents of which are hereby incorporated by reference in their entirety. In the methods provided herein, from two to about one thousand distinct antigen-binding molecules may be used. The term "distinct" is used herein to mean that each antigen-binding molecule binds a particular target antigen epitope. For example, between about 2 to about 500 distinct antigen-binding molecules, between about 2 to about 10 distinct antigen-binding molecules, between about 10 to about 50 distinct antigen-binding molecules, between about 50 to about 100 distinct antigen-binding molecules, between about 100 to about 200 distinct antigen-binding molecules, between about 200 to about 300 distinct antigen-binding molecules, between about 300 to about 400 distinct antigen-binding molecules, between about 400 to about 500 distinct antigen-binding molecules, or between about 500 to about 1,000 distinct antigen-binding molecules may be used in the methods provided. In the methods provided herein, the antigen-binding molecules may be added to or brought into contact with the cell-containing sample simultaneously or sequentially.

In some embodiments, the antigen-binding molecule may bind a particular covalent modification of a molecule, for example, a covalent modification of a protein. For example, the antigen-binding molecule may be an antigen-binding molecule that binds a phosphorylated amino acid on a protein or an antigen-binding molecule that binds a methylated or an acetylated amino acid on a protein. In another example, the antigen-binding molecule can be an antigen-binding molecule that binds a carbohydrate, lipid, acetyl group, formyl group, acyl group, SUMO protein, ubiquitin, Nedd, or prokaryotic ubiquitin-like protein on a protein of interest.

In the methods and compositions provided herein, antigen-binding molecules, for example, antibodies, are conjugated to an oligonucleotide. Oligonucleotides may be conjugated to an antigen-binding molecule by a number of methods known in the art (Kozlov et al. "Efficient strategies for the conjugation of oligonucleotides to antibodies enabling highly sensitive protein detection," *Biopolymers* 73(5): 621-630 (2004)). Aldehydes may be introduced into antibodies, for example, by modification of primary amines or oxidation of carbohydrate residues. Aldehyde- or hydrazine-modified oligonucleotides are prepared either during phosphoramidite synthesis or by post-synthesis derivatization. Conjugation between the modified oligonucleotide and antibody result in the formation of a hydrazone bond that is stable over long periods of time under physiological conditions. Oligonucleotides also may be conjugated to antibodies via a streptavidin/biotin bond, thiol/maleimide chemistry, azide/alkyne chemistry, tetrazine/cyclooctyne chemistry, and other click chemistries. These chemical handles are prepared either during phosphoramidite synthesis or post-synthesis. As used herein, the term "click chemistry" refers to biocompatible reactions intended primarily to join substrates of choice with specific biomolecules. Click chemistry reactions are not disturbed by water, generate minimal and non-toxic byproducts, and are characterized by a high thermodynamic driving force that drives it quickly and irreversibly to high yield of a single reaction product, with high reaction specificity.

In the methods and compositions provided herein, the oligonucleotide conjugated to each antigen-binding molecule includes a unique molecular identifier sequence, an antigen-binding molecule identifier sequence, and an assay molecular identifier sequence. The unique molecular identifier sequence can be between about five to about fifty nucleotides in length. For example, the molecular identifier sequence can be between about 5 and about 10, between about 10 and about 20, between about 20 and about 30, between about 30 and about 40, or between about 40 and about 50 nucleotides in length. The term "unique molecular identifier sequence" refers to a sequence that can be used to identify a specific oligonucleotide through amplification and/or sequencing methods. The use of unique molecular identifier sequences (UMIs) for amplification and high throughput sequencing reduces bias in quantification of the sequences after amplification. Due to the high sequence diversity of UMIs, no two reads in the library should contain the same UMI, unless they are duplicated in the PCR process. Such duplicates are collapsed into one read so that an undistorted representation of the original pre-PCR library is obtained. Since the UMIs are part of the sequences of the oligonucleotides conjugated to the antigen-binding molecule, they are automatically incorporated into the sequencing library without additional tagging.

The term "antigen-binding molecule identifier sequence" refers to a sequence that corresponds to the unique target antigen that is bound by the antigen-binding molecule. This sequence may be used to identify the unique target antigen by using amplification and/or sequencing methods. The antigen-binding molecule identifier sequence may be between about five to about fifty nucleotides in length. For example, the antigen-binding molecule identifier sequence may be between about 5 and about 10, between about 10 and about 20, between about 20 and about 30, between about 30 and about 40, or between about 40 and about 50 nucleotides in length.

The term "assay molecular identifier sequence" refers to a sequence that distinguishes between and allows separation of sequencing reads for genomic DNA and sequencing reads for antigen-binding molecular identifier sequences during analysis. The assay molecular identifier sequence may be between about five to about fifty nucleotides in length. For example, the antigen-binding molecule identifier sequence may be between about 5 and about 10, between about 10 and about 20, between about 20 and about 30, between about 30 and about 40, or between about 40 and about 50 nucleotides in length.

Optionally, the oligonucleotide conjugated to the antigen-binding molecule may also contain one or more nucleic acid primers for amplification and/or sequencing, for example, PCR handles. Further, to prevent self-complementarity, optionally, the unique molecular identifier sequence, the antigen-molecule identifier sequence, one or more nucleic acid primers, and the assay molecular identifier sequence may be present on one or more oligonucleotides. For example, a first oligonucleotide containing a first PCR handle and the assay molecular identifier sequence may be conjugated to an antigen-binding molecule, and a second oligonucleotide may contain a second PCR handle and the reverse complement of the assay molecular identifier sequence. See, for example, FIG. 6. In this example, the cell-containing sample is contacted with the antigen-binding molecule conjugated to the first oligonucleotide, and the second oligonucleotide is added to the tagmentation buffer. During tagmentation of genomic DNA, the two oligos are simultaneously hybridized to one another, and during the first stage of PCR, the primers are extended to form a full duplex, allowing subsequent PCR amplification.

In the method provided herein, cells in the cell-containing sample are lysed to produce a cell lysate that includes the contents of the lysed cells, for example, proteins, nucleic acids, and fragments thereof. Some of the methods provided herein may comprise lysing a population of cells or individual cells with an agent that extracts proteins and nucleic acids from the cells. The nucleic acids can comprise DNA and/or RNA. In some embodiments, proteins extracted from the cells are analyzed to obtain proteomic information. In some embodiments, DNA extracted from the cells is analyzed to obtain genomic information. In some embodiments, RNA extracted from the cells is analyzed to obtain transcriptomic information.

Methods for lysing cells are known in the art and include, but are not limited to, mechanical disruption of cell membranes, for example, by repeated thawing and freezing, sonication, bead homogenization, pressure, or filtration. Cells can also be lysed with a solution containing a detergent, for example, including, but not limited to Triton X-100, Triton-X114, NP-40, Brij-35, Brij-58, Tween 20, Tween 80, Octyl glucoside, Octyl thioglucoside, sodium dodecyl sulfate (SDS), CHAPS, and CHAPSO, to name a few. Cells can also be lysed by heating the cells to about 70-90° C. In some embodiments, the cell-containing sample is treated with Proteinase K prior to or concurrently with the lysing of the cell or cells in the sample.

In some embodiments, genomic DNA in the cells is tagmented to produce multiple double-stranded genomic DNA fragments comprising an oligonucleotide adaptor sequence at the 5' end of the each genomic DNA fragment. Optionally, the cells are permeabilized prior to tagmentation. Optionally, tagmentation of genomic DNA occurs prior to cell lysis, during cell lysis, or after cell lysis. In some examples, native chromatin structure is preserved during lysis so that tagmentation can be done selectively at sites where the genomic DNA is accessible, for example, at open chromatin sites, to enrich for regulatory regions. As used throughout, "tagmentation" is a process by which nucleic acid sequences, for example, genomic DNA is fragmented and labeled with an oligonucleotide adaptor sequence. Generally, a transposase (e.g., the Tn5 transposase or variant thereof) binds to a double-stranded sequence and catalyzes simultaneous fragmentation of a double-stranded DNA sample and tagging of the fragments with sequences that are adjacent to the transposon end sequence (i.e., by "tagmentation"). Methods for tagmenting, as well as transposon end sequences, are well known in the art (See, e.g., Picelli et al., *Genome Res.* 2014 24: 033-40; Adey et al., *Genome Biol.* 2010 11:R119 and Caruccio et al., *Methods Mol. Biol.* 2011 733: 41-55, US2010/0120098 and US2013/0203605). Kits for performing tagmentation are commercially sold under the tradename NEXTERA™, by Illumina (San Diego, Calif.). During tagmentation, the "label" or "adaptor" that is attached to the double-stranded nucleic acid refers to a nucleic acid that can be joined, via a transposase-mediated reaction, to at least one strand of a double-stranded nucleic acid molecule. In some embodiments, the label or adaptor refers to a molecule that is at least partially double-stranded. An adaptor may be about 10 to about 150 bases in length, although adaptors outside of this range are contemplated. Optionally, the oligonucleotide label or adaptor includes a sequencing adaptor comprising a primer sequence for amplification. In some methods, the cDNA library generated from mRNA transcripts in the cell-containing sample is tagmented to produce multiple double-stranded cDNA fragments comprising an oligonucleotide adaptor sequence at the 5' end of each cDNA fragment. In any of the methods provided herein, a tagmented cDNA library may be amplified using primers containing index sequences, for example, Illumina index sequences.

In some embodiments, mRNA transcripts are isolated from the cell lysate to produce a first fraction comprising the mRNA transcripts and a second fraction comprising labelled genomic DNA fragments and the antigen-binding molecule bound antigens from the cell lysate. Optionally, the mRNA transcripts are isolated from the cell lysate by allowing hybridization of the mRNA transcripts in the cell lysate with beads comprising poly (dT) sequences. Optionally, the isolated mRNA transcripts in the first fraction are retained in the same compartment in which the mRNA transcripts were isolated. Optionally, the first fraction is retained in the same compartment in which the mRNA transcripts were isolated and the second fraction is separated into a different compartment. In some embodiments, the compartment may be a well of a tissue culture plate or a microfluidic droplet.

In some embodiments of the disclosed methods, single cells from a population of cells are separated into individual compartments. In some embodiments, separation of single cells into individual compartments includes distributing or sorting single cells into individual compartments. Optionally, the single cells can be lysed after separation into individual compartments. The number of individual compartments can range from about 10 to about 100,000 individual compartments. One of skill in the art would know how to separate the population of cells to ensure that at least about 10%, 20%, 30%, 40%, 50%, 60%, 70%, 80%, or 90% of the individual compartments contain a single cell. Optionally, at least about 90%, 95%, or 99% of the individual compartments contain a single cell. Optionally, less than 25%, 10% or 5% of the individual compartments contain more than one cell. Optionally, each individual compartment containing a single cell further includes an oligonucleotide including a unique cellular identifier sequence that corresponds to the single cell in each compartment. In some embodiments, the cellular identifier sequence corresponds to a well in a tissue culture plate. In the methods set forth herein, the unique cellular identifier sequence is between about five and about fifty nucleotides in length. For example, the cellular identifier sequence can be between about 5 and about 10, between about 10 and about 20, between about 20 and about 30, between about 30 and about 40, or between about 40 and about 50 nucleotides in length. In some embodiments, the oligonucleotide including a unique cellular identifier sequence is used to amplify the unique molecular identifier sequence(s) and/or the antibody identifier sequence(s) in each compartment.

In some embodiments, an expression profile, a transcriptional profile, and/or an epigenetic profile is identified for the single cell. In some embodiments, the single cells are separated into wells of a tissue culture plate. In some embodiments, the single cells separated into individual compartments are single cells from a subpopulation of the population of cells contacted with the plurality of antigen-binding molecules. In some embodiments, the subpopulation of cells is isolated from the population of cells contacted with the plurality of antigen-binding molecules prior to separating single cells of the subpopulation into individual compartments, for example, by FACS or MACS, to isolate one or more specific cell types from the population. Optionally, the cells can be sorted by expression of a specific marker. Optionally, the subpopulation of cells is a subpopulation wherein at least 90%, 95%, or 99% of the cells express a specific marker.

Some of the methods disclosed herein include analyzing amplified molecular identifier sequences and/or antibody identifier sequences to identify the expression profile of the cell-containing sample. Some of the methods disclosed herein include analyzing amplified genomic DNA fragments to identify the epigenetic profile of the cell-containing sample. Some of the methods disclosed herein include analyzing a cDNA library to identify the transcriptional profile of the cell-containing sample. Methods for analyzing nucleic acid sequences are known in the art. These include, but are not limited to, DNA sequencing, hybridization assays, microarray assays, primer extension assays, polymerase chain reaction (PCR) assays, including quantitative PCR, and ligase chain reaction assays.

In some embodiments, the unique molecular identifier sequences, the antibody identifier sequences, the assay molecule identifier sequences, the genomic DNA fragments, and/or cDNAs are optionally sequenced. Sequencing methods include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, Calif.), ion semiconductor sequencing, ligation sequencing, sequencing by synthesis (Illumina, San Diego, Ca), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, tunneling currents DNA sequencing, and any other DNA sequencing method identified in the future. One or more of the sequencing methods described herein can be used in high throughput sequencing methods. As used herein, the term "high throughput sequencing" refers to all methods related to sequencing nucleic acids where more than one nucleic acid sequence is sequenced at a given time.

Optionally, the amplification products from the first and second fractions are pooled prior to sequencing. In some embodiments, the sequences from a cell-containing sample are labeled or barcoded with an oligonucleotide tag during amplification to allow for deconvolution and matching of epigenetic, transcriptomic, and/or proteomic information from the cell-containing sample. For example, a sample-level barcode or oligonucleotide label may be introduced by a PCR primer during amplification, and a distinct primer pair may be used for each distinct cell-containing sample. Optionally, in methods for single-cell analysis, the pooled sequencing results are deconvoluted using the unique cellular identifier sequences to identify the expression profile, the transcriptional profile and/or the epigenetic profile of a single cell associated with each unique cellular identifier sequence.

In some embodiments, the unique molecular identifier sequences and antibody identifier sequences are quantified and analyzed to identify an expression profile of a cell-containing sample. Accordingly, some embodiments include quantifying the amplified unique molecular identifier sequences and antibody identifier sequences and correlating the quantified amplified unique molecular identifier sequences and antibody identifier sequences to the quantities of target antigens of interest in the cell-containing sample. In some embodiments, the genomic DNA fragments are quantified and analyzed to identify an epigenetic profile of a cell-containing sample. Accordingly, some embodiments include quantifying the amplified genomic DNA fragments. In some embodiments, the cDNA library is quantified and analyzed to identify a transcriptional profile of a cell-containing sample. Accordingly, some embodiments include quantifying the amplified cDNA library to determine the amount of one or more mRNAs expressed in the cell-containing sample.

Additional methods for the biochemical analysis of a cell-containing sample include methods for identifying an expression profile and an epigenetic profile of a cell-containing sample. Certain methods include the steps of a) contacting a cell-containing sample with a plurality of antigen-binding molecules under conditions that promote specific binding of the antigen-binding molecules to target antigens of the cells in the sample; wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, an (ii) an antigen-binding molecule identifier sequence corresponding to the unique target antigen; and (iii) an assay molecular identifier sequence; b) tagmenting genomic DNA in the cell lysate to produce a plurality of double-stranded genomic DNA fragments comprising an oligonucleotide adaptor sequence at the 5' end of each genomic DNA fragment; c) lysing the cells in the sample; d) amplifying (i) the unique molecular identifier sequences, (ii) the antigen-binding molecule identifier sequences and (iii) the assay molecular identifier sequences in the cell lysate; e) analyzing the amplified unique molecular identifier sequences, the antigen-binding molecule identifier sequences, and the assay molecular identifier sequences to identify at least one target antigen to identify the expression profile in the sample; and f) analyzing the tagmented genomic DNA fragments to identify the epigenetic profile of the sample.

In some embodiments, the method further comprises quantifying the amplified unique molecular identifier sequences, the antigen-binding molecule identifier sequences, and the assay molecular identifier sequences. In some embodiments, the method further comprises using solid phase reversible immobilization to isolate tagmented DNA fragments prior to amplification. In some embodiments, the tagmented genomic DNA fragments are amplified and/or sequenced using one or more primers that hybridize to the oligonucleotide adaptor sequence at the 5' end of each fragment. In some embodiments, analyzing comprises sequencing the amplified unique molecular identifier sequences, the antigen-binding molecule identifier sequences, the assay molecular identifier sequences, and the genomic fragments. In some embodiments, the amplification products are pooled prior to sequencing. In some embodiments, the antigen is a protein. In specific embodiments, the protein is a cell surface protein or an intracellular protein. In some embodiments, the expression of two or more proteins are identified. In some embodiments, amplification is performed by polymerase chain reaction (PCR). In some embodiments, sequencing comprises sequence by synthesis. In some embodiments, sequencing comprises high throughput sequencing. In some embodiments, the unique molecular identifier sequence is between about five and about fifty nucleotides in length. In some embodiments, the antigen-binding molecule identifier sequence is between about five and about fifty nucleotides in length. In some embodiments, the plurality of antigen-binding molecules comprises between two and about five hundred distinct antigen-binding molecules. In some embodiments, the cell-containing sample is treated with Proteinase K prior to or concurrently with the lysing of the cells in the sample. In some embodiments, the cell-containing sample is a population of cells. In some embodiments, single cells of the population are separated into individual compartments prior to lysing the single cell in each compartment. In some embodiments, an expression profile and an epigenetic profile are identified for the single cell. In some embodiments, the individual compartments are wells of a tissue culture plate. In some embodiments, the single cells separated into individual compartments are single cells from a subpopulation of the population of cells contacted with the plurality of antigen-binding molecules. In some embodiments, the subpopulation of cells is isolated from the population of cells contacted with the plurality of antigen-binding molecules prior to separating single cells of the subpopulation into individual compartments. In some embodiments, the subpopulation is isolated using FACS or MACS. In some embodiments, the antigen-binding molecule is an antibody.

Additional methods for the biochemical analysis of a cell-containing sample include methods for identifying a transcriptional profile and an epigenetic profile of a cell-containing sample. Certain methods include the steps of a) tagmenting genomic DNA in the cells in the sample to produce a plurality of double-stranded genomic DNA fragments comprising an oligonucleotide adaptor sequence at the 5' end of each genomic DNA fragment; b) lysing the cells; c) isolating mRNA transcripts from the cell lysate to produce a first fraction comprising the mRNA transcripts and a second fraction comprising the tagmented genomic DNA fragments; d) generating a cDNA library by reverse transcribing the mRNA transcripts in the first fraction; e) amplifying the tagmented genomic DNA fragments in the second fraction; f) analyzing the tagmented genomic DNA fragments in the second fraction to identify the epigenetic profile of the sample; and g) analyzing the cDNA library generated from the first fraction to identify the transcriptional profile of the sample. In some embodiments, the cells are permeabilized prior to tagmentation of the genomic DNA fragments.

In some embodiments, the method further comprises using solid phase reversible immobilization to isolate DNA fragments prior to amplification. In some embodiments, the genomic DNA fragments are amplified and/or sequenced using one or more primers that hybridize to the oligonucleotide adaptor sequence at the 5' end of each tagmented genomic DNA fragment. In some embodiments, the amplification products are pooled prior to sequencing. In some embodiments, amplification is performed by polymerase chain reaction (PCR). In some embodiments, sequencing comprises sequence by synthesis. In some embodiments, sequencing comprises high throughput sequencing. In some embodiments, the cell-containing sample is a population of cells. In some embodiments, single cells of the population are separated into individual compartments prior to lysing the single cell in each compartment. In some embodiments, an epigenetic profile and a transcriptional profile are identified for the single cell. In some embodiments, the individual compartments are wells of a tissue culture plate. In some embodiments, the single cells separated into individual compartments are single cells from a subpopulation of the population of cells. In some embodiments, the subpopulation of cells is isolated from the population of cells prior to separating single cells of the subpopulation into individual compartments. In some embodiments, the subpopulation is isolated using FACS or MACS.

Disclosed are materials, compositions, and components that can be used for, can be used in conjunction with, can be used in preparation for, or are products of the disclosed embodiments. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. The following description provides further non-limiting examples of the disclosed compositions and methods.

EXAMPLES

Example 1

Cell Staining with Fluorescent Antibodies and Oligo-Linked Antibodies

A vial of peripheral blood mononuclear cells (PBMCs) (about 8 million cells/ml, at 90% viability) was thawed. The thawed cells were washed with FACS buffer (95% Dulbecco Phosphate Buffered Saline (DPBS) and 5% fetal bovine serum (FBS)). The cells were counted and washed one time with FACS buffer. Then, the cells were resuspended in 50 μL of FACS buffer that included 10 μg/ml of yeast tRNA (five μg/ml after adding 50 μL of stain cocktail). The cells were contacted with 50 μL of antibody staining cocktail, including the fluorescent antibody used for FACS and about 0.05 μg of each oligo-conjugated antibody, and incubated in the dark, at 4° C., for 30 minutes. After incubation, the cells were washed one time in FACS buffer. The cells were resuspended in FACS buffer and strained through a 5 ml polystyrene tube with a 40 μm strainer. Each oligo-conjugated antibody comprised an oligonucleotide that included a PCR primer and an assay molecular identifier sequence. A second oligonucleotide comprising a PCR primer, an antigen-binding molecule identifier sequence, a unique molecular identifier sequence, and the reverse complement of the assay molecular identifier sequence was added during tagmentation as described above. For the structure of the oligonucleotides, see FIG. 6.

Example 2

FACS Sorting into Subsets and ATAC Tagmentation

Bulk sorts for T4, T8, CD5610 CD3-, and CD14/CD19+ CD91− cell populations were performed. Populations of 1) CD3+CD4+CD8-, 2) CD3+CD4− CD8+, 3) CD19+CD91−, and 4) CD5610 CD3− cells were sorted.

Using the T4 subset tube, the cells were sorted into an appropriate tube/plate format containing an ATAC/Immuno-PCR reaction mix (Table 1) that was prepared ahead of time.

TABLE 1

| Components in the ATAC/Immuno-PCR reaction mix | Vol per rxn (μl) |
|---|---|
| 2X TD buffer | 10 |
| 10% NP-40 | 0.2 |
| $H_2O$ | 5.8 |
| Tagment DNA Enzyme (TDE1) | 2 |
| RNAseOUT | 1 |
| ImmunoPCR universal forward primer @ 1 μM | 1 |
| total | 20 |

After eight tubes were sorted, the genomic DNA in the cells was tagmented for 30 minutes at 37° C., on a thermomixer, at 500 rpm. The tagmented fluid tubes were transferred to a 96×0.5 ml Coolrack on dry ice to snap freeze for at least 5 minutes.

Three μl of a proteinase K and sodium dodecyl sulfate mix (Table 2) was added to each tube.

TABLE 2

| | 1 rxn, (μl) |
|---|---|
| pK (20 mg/ml) | 1 |
| SDS (10%) | 2 |
| qs w/sample | 20 |
| | 23 |

The mixture was pipetted up and down, followed by incubation at 55° C., for 30 minutes. After incubation, 7 μl of 4.167M LiCL/83.3 M EDTA was added to each sample and vortexed for 30 seconds before spinning down.

Example 3

Separation of RNA and Tagmented DNA

RNA was separated from the other components, including tagmented DNA and antigens bound by barcoded antibodies in the cell-containing samples, for further analysis. Four of well-mixed oligodTVN beads were aliquoted into each well of a LoBind plate. The plate was put on a DynaMag™-96 Side Skirted Magnet for 30 seconds, or until the supernatant was clear. The supernatant was aspirated and the plate was removed from the magnet. The beads were resuspended with the lysed cells (30 Hybridization, for 30 minutes at 25° C. and 2000 rpm, was performed on the Eppendorf Thermomixer C. Samples were removed from the Thermomixer C and spun down. The plate was placed on the magnet for two minutes. The supernatant was transferred into a new plate for ATACseq (genomic profiling) and ImmunoPCR (expression profiling) analysis. The plate containing the RNA samples was stored on ice if it was processed soon or stored at −20° C. for later processing. From this point on, the ATAC & ImmunoPCR and RNA samples were processed separately.

Example 4

ATACseq & ImmunoPCR

A 2.83× (volume/volume) SPRIselect® bead cleanup was performed, and the sample was eluted in 25 μL of Buffer EB (Table 3) prior to performing PCR. PCR cycle settings are shown in Table 4.

TABLE 3

| | 1 rxn |
|---|---|
| Fidelity buffer (5x) | 10 |
| 10 mM dNTP | 1.5 |
| KAPA HIFI DNA polymerase (1 U/ul) | 1 |
| Nuclease Free $H_2O$ | 10 |
| 15 primer | 1.25 |
| 17 primer | 1.25 |
| Eluted Sample | 25 |
| total | 50 |

TABLE 4

| Step | Cycle | Temp (° C.) | Time | Purpose |
|---|---|---|---|---|
| 1 | | 72 | 3 minutes | Extension |
| 2 | | 95 | 3 minutes | Initial Denaturing |
| 3 | 15 | 95 | 20 s | Denaturing |
| 4 | | 63 | 15 s | Anneal |
| 5 | | 72 | 60 s | Extension |
| 6 | | 72 | 5 min | Final extension |
| 7 | | 4 | Hold | Hold |

A 1.2× (volume/volume) SPRIselect bead cleanup was performed. The sample was eluted in Buffer EB, quantitated using qPCR, pooled, and sequenced.

Example 5

RNAseq

The bead plates obtained after separating RNA from tagmented DNA and antibody-labeled proteins were washed twice in 80% ethanol and eluted in 4 μL of dNTP buffer (Table 5).

TABLE 5

| Component | Volume Per Sample (μL) | Mastermix Volume (μL) |
|---|---|---|
| 0.01% TWEEN20 | 3 | =3 * n |
| dNTP (10 mM) | 1 | =1 * n |
| Total | 4 | =4 * n |

The plates were incubated on a ThermoMixer C at 2000 rpm, at 25° C. for two minutes. The samples were then denatured at 75° C. for two minutes as per the protocol in Table 6.

TABLE 6

| Step | Temp (° C.) | Time | Purpose |
|---|---|---|---|
| 1 | 75 | Infinite | Preheating Thermocycler. Hit "ENTER" to skip step upon loading samples. |
| 2 | 75 | 2 minutes | Denature secondary structures |
| 3 | 4 | Hold | Hold |

Lid temperature = 105° C.
Total volume = 4 μL.

The plates were incubated on ice for at least three minutes while the reverse transcriptase (RT) mastermix (Table 7) was prepared.

TABLE 7

| Component | Volume (μL) | Mastermix Volume (μL) |
|---|---|---|
| Nuclease free water | 0.34 | = 0.34 * n |
| Superscript II first strand buffer | 2 | = 2 * n |
| 100 mM DTT | 0.5 | = 0.5 * n |
| 1M $MgCl_2$ | 0.06 | = 0.06 * n |
| 5M Betaine | 2 | = 2 * n |
| 100 mM Template Switching Oligo (TSO) | 0.1 | = 0.1 * n |
| RNaseOUT Recombinant Ribonuclease Inhibitor | 0.5 | = 0.5 * n |
| Superscript II reverse transcriptase | 0.5 | = 0.5 * n |
| Final Volume | 6 | = 6 * n |

Six μL of RT mastermix were added to each sample. The sample was pipetted up and down ten times to mix well. The sample was pulse spun for 3 seconds to collect all liquid at the bottom. The RT program (Table 8) was run on the thermocycler.

TABLE 8

| Step | Cycle | Temp (° C.) | Time | Purpose |
|---|---|---|---|---|
| 1 | | 42 | Infinite | Preheating thermocycler. Hit "ENTER" upon loading samples. |
| 2 | | 42 | 180 minutes | RT and template switching |
| 3 | Steps 3-4 cycle 10× | 50 | 2 minutes | Unfolding RNA |
| 4 | | 42 | 2 minutes | Completion/continuation of RT and template switching |
| 5 | | 70 | 15 minutes | Enzyme inactivation |
| 6 | | 4 | Hold | Storage |

Lid temperature = 60° C.
Total volume = 10 μL.

Twenty minutes before the RT programs ended, a whole transcriptome amplification (WTA) mastermix was prepared (Table 9).

TABLE 9

| Component | Volume (μL) | Mastermix Volume (μL) |
|---|---|---|
| KAPA HiFi Hotstart ReadyMix (2×) | 12.5 | = 12.5 * n |
| 10 μM ISPCR primers | 0.25 | = 0.25 * n |
| Nuclease free water | 2.25 | = 2.25 * n |
| Total volume | 15 | = 15 * n |

Once the RT program finished, the samples were taken out and spun down at 2000 rcf for 1 minute. 15 μL of the master mix was added to the wells. The mixture was pipetted up and down to mix thoroughly and pulse spun for 3 seconds. The WTA protocol (Table 10) was run.

TABLE 10

| Step | Cycle | Temp (° C.) | Time | Purpose |
|---|---|---|---|---|
| 1 | | 98 | Infinite | Preheating thermocycler. Hit "ENTER" upon loading samples. |
| 2 | | 98 | 3 minutes | Denature |
| 3 | | 98 | 20 seconds | Denature |
| 4 | Steps 3-5 cycle 18× | 67 | 15 seconds | Anneal |
| 5 | | 72 | 6 minutes | Extend |
| 6 | | 72 | 5 minutes | Extend |
| 7 | | 4 | Hold | Storage |

Lid temperature = 105° C.
Total volume = 25 μ L.

Once the program finished, the samples were taken out and spun down at 2000 rcf for 1 minute. A 0.6× (volume/volume) SPRIselect® bead cleanup was performed, and the sample was eluted in 25 μL EB. The cleaned up cDNA was quantitated. The samples were diluted to 0.15 ng/μL. The Nextera mastermix was made (Table 11).

TABLE 11

| Component | Volume (μL) | Mastermix Volume (μL) |
|---|---|---|
| Tagmentation DNA buffer (TD) | 2.5 | = 2.5 * 11 |
| Amplicon tagment mix (ATM) | 1.25 | = 1.25 * n |
| Total | 3.75 | = 3.75 * n |

Then 3.75 μL of the Nextera mastermix per well was aliquoted in a new LoBind plate, and 1.25 μL of 0.15 cDNA was added, mixed well, and spun down at 2000 rcf for 1 minute. The samples were placed in the thermocycler on the Nextera XT tagmentation program (Table 12).

TABLE 12

| Step | Temperature (° C.) | Time | Purpose |
|---|---|---|---|
| 1 | 55 | Hold | Preheating thermocycler. Hit "ENTER" upon loading samples. |
| 2 | 55 | 10 m | Tagmentation |
| 3 | 4 | Hold | Storage |

Lid temperature = 105° C.
Total volume = 5 μL

Once the program finished, the samples were taken out and spun down at 2000 rcf for 1 minute, and 1.25 μL NT buffer was added to the tagmented samples. The samples were mixed well, and incubated at room temperature for 5 minutes. 2.5 μL of unique Nextera primers (1.25 μL each of i7 and i5) and 3.75 μL Nextera PCR Mastermix (NPM) were added to each sample and mixed well prior to running the Nextera PCR Program (Table 13).

TABLE 13

| Step | Cycle | Temp (° C.) | Time | Purpose |
|---|---|---|---|---|
| 1 | | 72 | Infinite | Preheating thermocycler. Hit "ENTER" upon loading samples. |
| 2 | | 72 | 3 min | Remove secondary structures |
| 3 | | 95 | 30 s | Initial Denaturing |
| 4 | Steps 3- | 95 | 10 s | Denaturing |
| 5 | 5 cycle 12× | 55 | 30 s | Anneal |
| 6 | | 72 | 60 s | Extension |
| 7 | | 72 | 5 min | Final extension |
| 8 | | 4 | hold | Storage |

Lid temperature = 105° C.
Total volume = 12.5 μL.

A 0.6× (volume/volume) SPRIselect bead cleanup was performed and the sample was. eluted in 25 μL Buffer EB before quantitate with qPCR, pooling, and sequencing.

Example 6

Results of Transcriptional, Epigenetic, and Expression Profiling

Cell-containing samples that included two subsets of cells (subset 1: CD3+CD4+, and subset 2: CD19+) were analyzed using the procedures as described in Examples 1 through 4. The transcription profile, epigenetic profile, and expression profile were determined, and representative results are shown in FIGS. 1 through 5. Library preps from each sample were carried out in separate compartments (e.g. separate wells on a multi-well plate), allowing a sample-level barcoding during PCR library amplification. In this way, all ATAC and ImmunoPCR reads (PCR amplified together since they have compatible PCR primer sites) carry sample specific barcodes, and can be assigned back to the correct sample after next generation sequencing. Then, sample-data relationships were tracked by file name and folder structure organization.

RNAseq (Transcriptional Profiling)

RNAseq was performed as described above. Two subsets of cells (subset 1: CD3+CD4+, and subset 2: CD19+) were sequenced, and the RNA expression correlation for RNAseq between the subsets and between replicates of each subset is show in FIG. 1. The samples are listed along the left and top of the figure. The samples are listed by the following nomenclature: "Sample [subset ID #] [replicate #]." The correlation among technical replicates (e.g, between samples 3A-3G, or between samples 1B-1G) is higher than correlation between different cell types (e.g., between a replicate of subset 1 and a replicate of subset 2).

Figure 2:
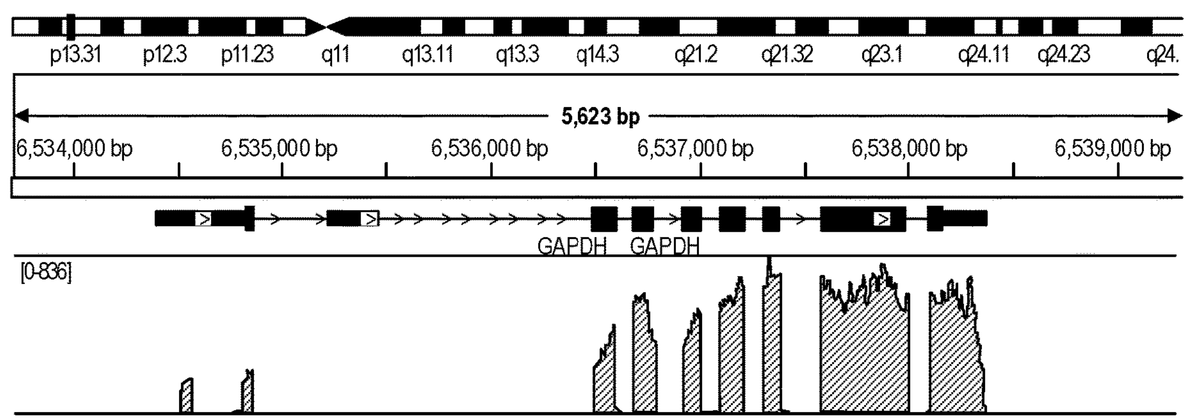
FIG. 2 shows an IgV snapshot of GAPDH, a housekeeping gene. Clean coverage of reads over exonic regions is shown. RNAseq detected abundant reads (shown in grey at the bottom of the figure) covering exonic regions (shown as thick bars in the middle of the figure) of the housekeeping gene GAPDH. Colored bars in the top of the figure indicate single nucleotide variants from reference genome.

FIG. 2 shows an IgV snapshot of a housekeeping gene, GAPDH. The figure shows that there was clean coverage of reads over each of the exonic regions in this housekeeping gene. This demonstrates that the mRNA of this housekeeping gene was present as expected in the cell-containing sample.

ATAC (Genomic Profiling)

ATACseq was performed as described in the previous examples, and the correlation of the results obtained with replicates of each subset are shown in FIG. 3. The samples are listed along the left and top of the figure. The samples are listed by the following nomenclature: "Sample [subset ID #] [replicate #]." Peak Correlation between sample replicates for ATACseq is about 0.9 for a good sample. In FIG. 3, the correlation between replicates of subset 1 is about 0.87. Correlation between replicates of subset 2 is about 0.88. Since subset 1 and subset 2 are two distinct subsets, correlation between samples of subset 1 and subset 2 is expected to be low, which is consistent with the data observed (correlation was about 0.5 between replicates of different subsets).

Figure 4:
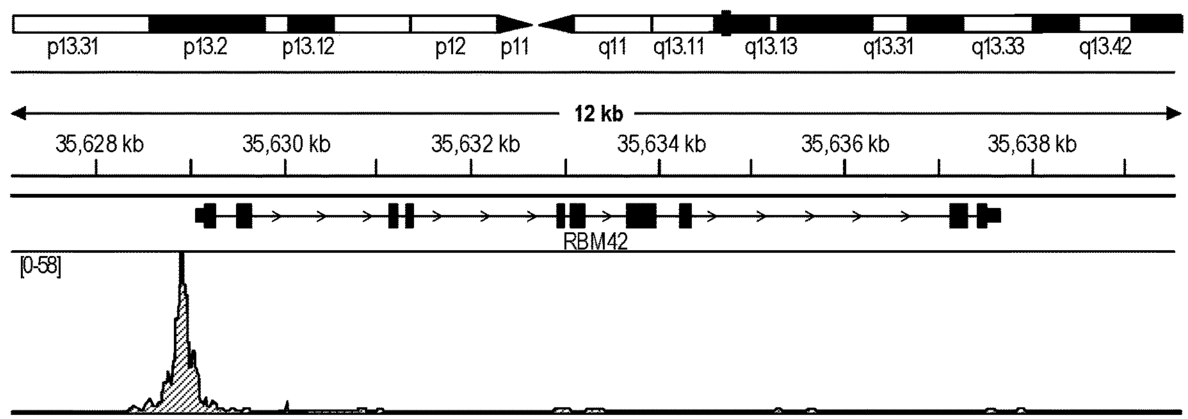
FIG. 4 is an IgV Snapshot of RBM42. High enrichment of reads (pileup in the peak shape) at the promoter of this active gene, indicating open chromatin, is shown. ATACseq detected abundant reads (shown in grey) covering the open-chromatin promoter regions immediately upstream to RBM42, an actively transcribed gene.

FIG. 4 is a graph showing an IgV snapshot of RBM42. The figure shows a high enrichment of reads (pileup in the peak shape) at the promoter of this active gene, indicating open chromatin. RBM42 has a constitutively active promoter among all PBMC subsets analyzed. Hence, this promoter was chosen as a housekeeping locus for quality control purposes.

ImmunoPCR (Expression Profiling)

Figure 5:
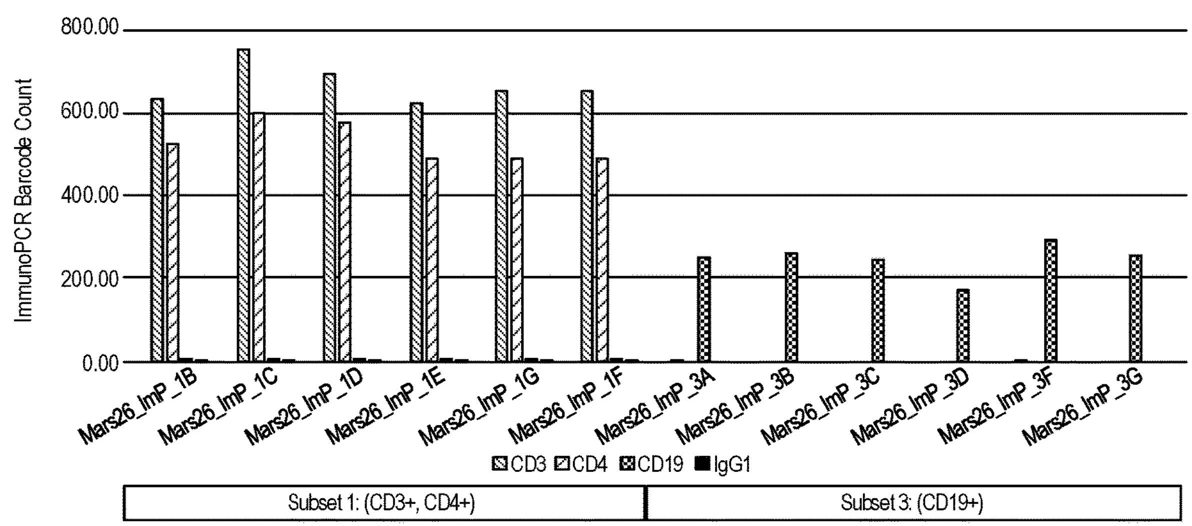
FIG. 5 is a graph showing the results of expression profiling. The graph shows the barcode counts for each oligonucleotide-labeled antibody. The sequencing data for the oligonucleotides conjugated to the antibodies correlates well to expected markers of each subset. Subset 1 should consist of cell population that is both $CD3^+$ and $CD4^+$, and the CD3 and CD4 barcode counts for subset 1 replicates are both high with low to no signal from CD19 or IgG1 barcodes. Subset 2 should consist of cell population that is only $CD19^+$, and the CD19 barcode counts of subset 2 replicates are high with low to no signal from any other oligo-Antibody. Sample replicate to replicate variability is low, which supports the reproducibility of the method.

ImmunoPCR was performed as described above with each antibody labeled with a different oligonucleotide label or barcode. FIG. 5 is a graph of the ImmunoPCR barcode counts present for each of four different oligo-labeled antibodies in the cells tested. The left side of the graph shows results obtained with replicates of subset 1, and the right side of the graph shows results obtained with replicates of subset 2. For each replicate tested, the counts of each barcode were determine and are for CD3, CD4, CD19, and IgG1, shown from left to right for each replicate listed. The ImmunoPCR sequencing data correlates well with the expected markers of each cell subset. Subset 1 should consist of a cell population that is both CD3+ and CD4+, and the CD3 and CD4 barcode counts for subset 1 replicates are both high with low to no signal from CD19 or IgG1. Subset 2 should consist of a cell population that is only CD19+, and the CD19 barcode counts of subset 2 replicates are high with low to no signal from any other oligo-labeled antibody. Sample replicate to replicate variability is low, which supports the reproducibility of the assay.

These experiments show that an expression profile, a transcriptional profile, and an epigenetic profile can be simultaneously identified from the same cell-containing sample.

What is claimed is:

1. A method for biochemical analysis of a cell-containing sample, comprising:

a) contacting a cell-containing sample with a plurality of antigen-binding molecules under conditions that promote specific binding of the antigen-binding molecules to target antigens of the cells in the sample; wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, (ii) an antigen-binding molecule identifier sequence corresponding to the unique target antigen, and (iii) an assay molecular identifier sequence;

b) tagmenting genomic DNA in the cells to produce a plurality of double-stranded genomic DNA fragments comprising an oligonucleotide adaptor sequence at the 5' end of each genomic DNA fragment;

c) lysing the cells in the sample;

d) isolating mRNA transcripts from the cell lysate to produce a first fraction comprising the mRNA transcripts and a second fraction comprising tagmented genomic DNA fragments and the antigen-binding molecule-bound antigens from the cell lysate;

e) generating a cDNA library by reverse transcribing the mRNA transcripts in the first fraction;

f) amplifying (i) the unique molecular identifier sequences; (ii) the antigen-binding molecule identifier sequences; (iii) the assay molecular identifier sequences, and the (iv) tagmented genomic DNA fragments in the second fraction;

g) analyzing the amplified unique molecular identifier sequences, the assay molecular identifier sequences, and the antigen-binding molecule identifier sequences to identify at least one target antigen in the second fraction to identify the expression profile of the sample;

h) analyzing the tagmented genomic DNA fragments in the second fraction to identify the epigenetic profile of the sample; and i) analyzing the cDNA library generated from the first fraction to identify the transcriptional profile of the sample.

2. The method of claim 1, further comprising quantifying the amplified unique molecular identifier sequences, antigen-binding molecule identifier sequences and the genomic DNA fragments in the second fraction.

3. The method of claim 1, wherein analyzing in step g) and step h) comprises sequencing the amplified unique molecular identifier sequences, the antigen-binding molecule identifier sequences, the assay molecular identifier sequences, and the tagmented genomic fragments in the second fraction.

4. The method of claim 1, wherein the antigen is a protein.

5. The method of claim 4, wherein the expression of two or more proteins are identified.

6. The method of claim 1, wherein the method further comprises tagmenting the cDNA library to produce a plurality of double-stranded cDNA fragments comprising an oligonucleotide adaptor sequence at the 5' end of each cDNA prior to analyzing.

7. The method of claim 1, wherein the cell-containing sample is a population of cells.

8. The method of claim 7, wherein single cells of the population are separated into individual compartments prior to lysing the single cell in each compartment.

9. The method of claim 8, wherein an expression profile, an epigenetic profile and a transcriptional profile are identified for the single cell.

10. The method of claim 8, wherein the single cells separated into individual compartments are single cells from a subpopulation of the population of cells contacted with the plurality of antigen-binding molecules.

11. The method of claim 10, wherein the subpopulation of cells is isolated from the population of cells contacted with the plurality of antigen-binding molecules prior to separating.

12. The method of claim 1, wherein the antigen-binding molecule is an antibody.

13. A method for biochemical analysis of a cell-containing sample, comprising:

a) contacting a cell-containing sample with a plurality of antigen-binding molecules under conditions that promote specific binding of the antigen-binding molecules to target antigens of the cells in the sample; wherein each antigen-binding molecule in the plurality binds to a unique target antigen in one or more cells of the sample, wherein each antigen-binding molecule is conjugated to an oligonucleotide, and wherein the oligonucleotide comprises (i) a unique molecular identifier sequence, (ii) an antigen-binding molecule identifier sequence corresponding to the unique target antigen, and (iii) an assay molecular identifier sequence;

b) tagmenting genomic DNA in the cell lysate to produce a plurality of double-stranded genomic DNA fragments comprising an oligonucleotide adaptor sequence at the 5' end of each genomic DNA fragment;

c) lysing the cells in the sample;

d) amplifying (i) the unique molecular identifier sequences, (ii) the antigen-binding molecule identifier sequences, and (iii) the assay molecular identifier sequence in the cell lysate;

e) analyzing the amplified unique molecular identifier sequences and antigen-binding molecule identifier sequences to identify at least one target antigen to identify the expression profile in the sample; and f) analyzing the genomic DNA fragments to identify the epigenetic profile of the sample.

14. The method of claim 13, further comprising quantifying the amplified unique molecular identifier sequences and antigen-binding molecule identifier sequences.

15. The method of claim 13, wherein analyzing comprises sequencing the amplified unique molecular identifier sequences, the antigen-binding molecule identifier sequences, the assay molecular identifier sequences, and the tagmented genomic fragments.

16. The method of claim 13, wherein the antigen is a protein.

17. The method of claim 16, wherein the expression of two or more proteins are identified.

18. The method of claim 13, wherein the cell-containing sample is a population of cells.

19. The method of claim 18, wherein single cells of the population are separated into individual compartments prior to lysing the single cell in each compartment.

20. The method of claim 19, wherein an expression profile and an epigenetic profile are identified for the single cell.

21. The method claim 19, wherein the single cells separated into individual compartments are single cells from a subpopulation of the population of cells contacted with the plurality of antigen-binding molecules.

22. The method of claim 13, wherein the antigen-binding molecule is an antibody.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial sequence
<220> FEATURE:
<223> OTHER INFORMATION: Synthetic construct

<400> SEQUENCE: 1

tcgtcggcag cgtcagatgt gtataagaga caggcagtgt gccttcattc              50


<210> SEQ ID NO 2
<211> LENGTH: 65
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (35)..(48)
<223> OTHER INFORMATION: n is a, c, g, or t

<400> SEQUENCE: 2

gtctcgtggg ctcggagatg tgtataagag acagnnnnnn nnnnnnnnga atgaaggcac     60

actgc                                                                 65
```